United States Patent
Pedrazzini

(10) Patent No.: US 8,037,993 B2
(45) Date of Patent: Oct. 18, 2011

(54) CONTAINER CARRIER TURNING DEVICE FOR A CONTAINER CARRIER CONVEYOR

(75) Inventor: Glanandrea Pedrazzini, Paradiso (CH)

(73) Assignee: Inpeco IP Ltd., Valletta (MT)

( * ) Notice: Subject to any disclaimer, the term of this patent is extended or adjusted under 35 U.S.C. 154(b) by 40 days.

(21) Appl. No.: 12/517,476

(22) PCT Filed: Dec. 4, 2006

(86) PCT No.: PCT/EP2006/069275
§ 371 (c)(1),
(2), (4) Date: Sep. 2, 2009

(87) PCT Pub. No.: WO2008/067845
PCT Pub. Date: Jun. 12, 2008

(65) Prior Publication Data
US 2010/0012460 A1    Jan. 21, 2010

(51) Int. Cl.
*B65G 47/244* (2006.01)
*G06K 13/107* (2006.01)
(52) U.S. Cl. .................. 198/394; 198/416; 198/459.6
(58) Field of Classification Search .................. 198/394, 198/401, 416, 459.06, 465.1, 597
See application file for complete search history.

(56) References Cited

U.S. PATENT DOCUMENTS

| | | | | |
|---|---|---|---|---|
| 3,941,686 A | * | 3/1976 | Juvinall | 209/523 |
| 4,915,237 A | * | 4/1990 | Chang et al. | 209/524 |
| 5,127,509 A | * | 7/1992 | Kohlen et al. | 198/345.3 |
| 5,730,276 A | * | 3/1998 | Itoh | 198/465.1 |
| 5,810,955 A | * | 9/1998 | Seifert et al. | 156/64 |
| 5,941,366 A | * | 8/1999 | Quinlan et al. | 198/465.1 |
| 6,298,974 B1 | * | 10/2001 | Heuft et al. | 198/339.1 |
| 6,343,690 B1 | * | 2/2002 | Britton et al. | 198/867.06 |
| 6,413,780 B1 | * | 7/2002 | Bach et al. | 436/48 |
| 6,520,313 B1 | * | 2/2003 | Kaarakainen et al. | 198/369.5 |
| 6,550,512 B2 | * | 4/2003 | Yang | 156/351 |
| 7,673,736 B2 | * | 3/2010 | Kowalchuk | 198/478.1 |

FOREIGN PATENT DOCUMENTS

| | | |
|---|---|---|
| EP | 0 479 622 A1 | 4/1992 |
| EP | 0 639 774 A1 | 2/1995 |
| EP | 0 727 665 A2 | 8/1996 |

* cited by examiner

*Primary Examiner* — Douglas Hess
(74) *Attorney, Agent, or Firm* — Birch, Stewart, Kolasch & Birch, LLP

(57) ABSTRACT

A container carrier turning device for a specimen container provided with an ID barcode and inserted into a carrier made advancing by a conveyor belt. The turning device includes a carrier stopping arrangement for rotatably engaging a lateral surface of the carrier to stop the advancing movement of the carrier while leaving it free to rotate around the container axis, and a carrier pressing arrangement for rotatably engaging an upper surface of the carrier. An elastic arrangement forces the carrier pressing arrangement to a carrier engaging position. An idle bearing, opposite to the carrier stopping arrangement, facilitates the carrier rotation. An RFID antenna is associated with the carrier turning device to identify a container carrier tag.

2 Claims, 6 Drawing Sheets

CONTAINER CARRIER TURNING DEVICE FOR A CONTAINER CARRIER CONVEYOR

The present invention concerns a container carrier turning device which can be used in a container carrier conveyor for reading the container identifying (ID) barcode.

As used herein, the term "container" means an article that contains a biological specimen and has a tubular opening for access of the contents, e.g. a test tube.

In automated clinical chemistry laboratories, specimen containers provided with an identifying barcode are inserted into respective carriers moved on a conveyor belt through a succession of process stations.

At the entry into a workcell it is necessary to check the ID of the specimen container by means of a barcode reader, which is in a fixed position while the barcode on the container may be in a position which does not allow its reading by the barcode reader.

In that case it is necessary to turn the container around its axis until the barcode reaches a position in front of the barcode reader.

Object of the present invention is to provide a container carrier turning device which does not need a specific driving motor.

According to the invention said object is achieved by a container carrier turning device for a specimen container provided with an ID barcode and inserted into a carrier that moves on a conveyor belt, characterized by comprising carrier stopping means for rotatably engaging a lateral surface of said carrier to stop the advancing movement of the carrier while leaving it free to rotate around the container axis, carrier pressing means for rotatably engaging an upper surface of said carrier, elastic means for forcing said carrier pressing means to a carrier engaging position, first pneumatic means for moving said carrier stopping means to a carrier stopping position and second pneumatic means for moving said carrier pressing means to a carrier disengaging position against the action of said elastic means.

In other words when driven by the first pneumatic means the carrier stopping means stop the advancing movement of the container carrier while the conveyor belt prosecutes its run. The second pneumatic means allow the elastic means to force the carrier pressing means onto the upper surface of the container carrier. As a consequence, the running conveyor belt causes a rotation of the container carrier until the container barcode reaches the proper position that allows the reading of the container ID by the barcode reader. The second pneumatic means then allow the carrier pressing means to disengage from the upper surface of the container carrier stopping the carrier rotation and the first pneumatic means then allow the carrier stopping means to disengage from the lateral surface of the container carrier leaving the container carrier to advance again on the conveyor belt.

The characteristics and advantages of the present invention will appear evident from the following detailed description of an embodiment thereof illustrated as non-limiting example in the enclosed drawings, in which.

Figure 1:
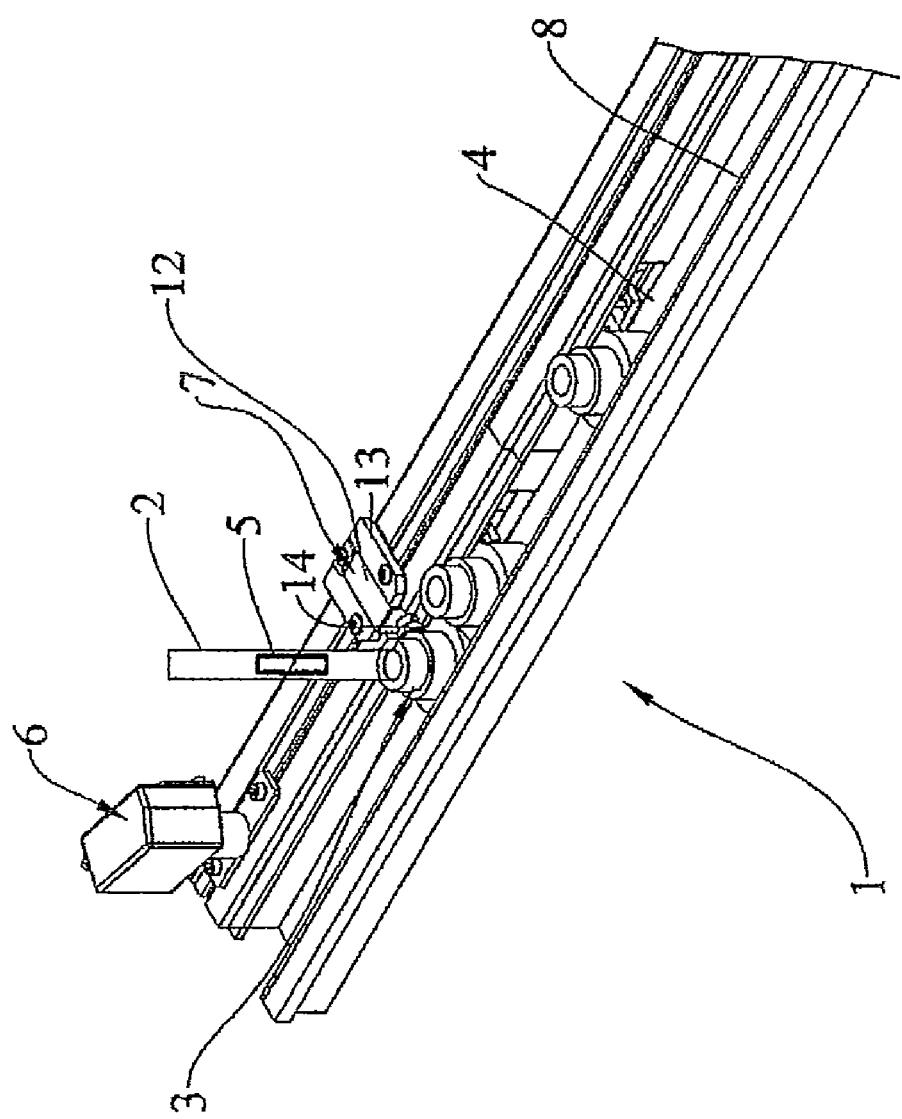
FIG. 1 is a perspective view of a conveyor portion comprising a turning device according to the present invention.
Figure 2:
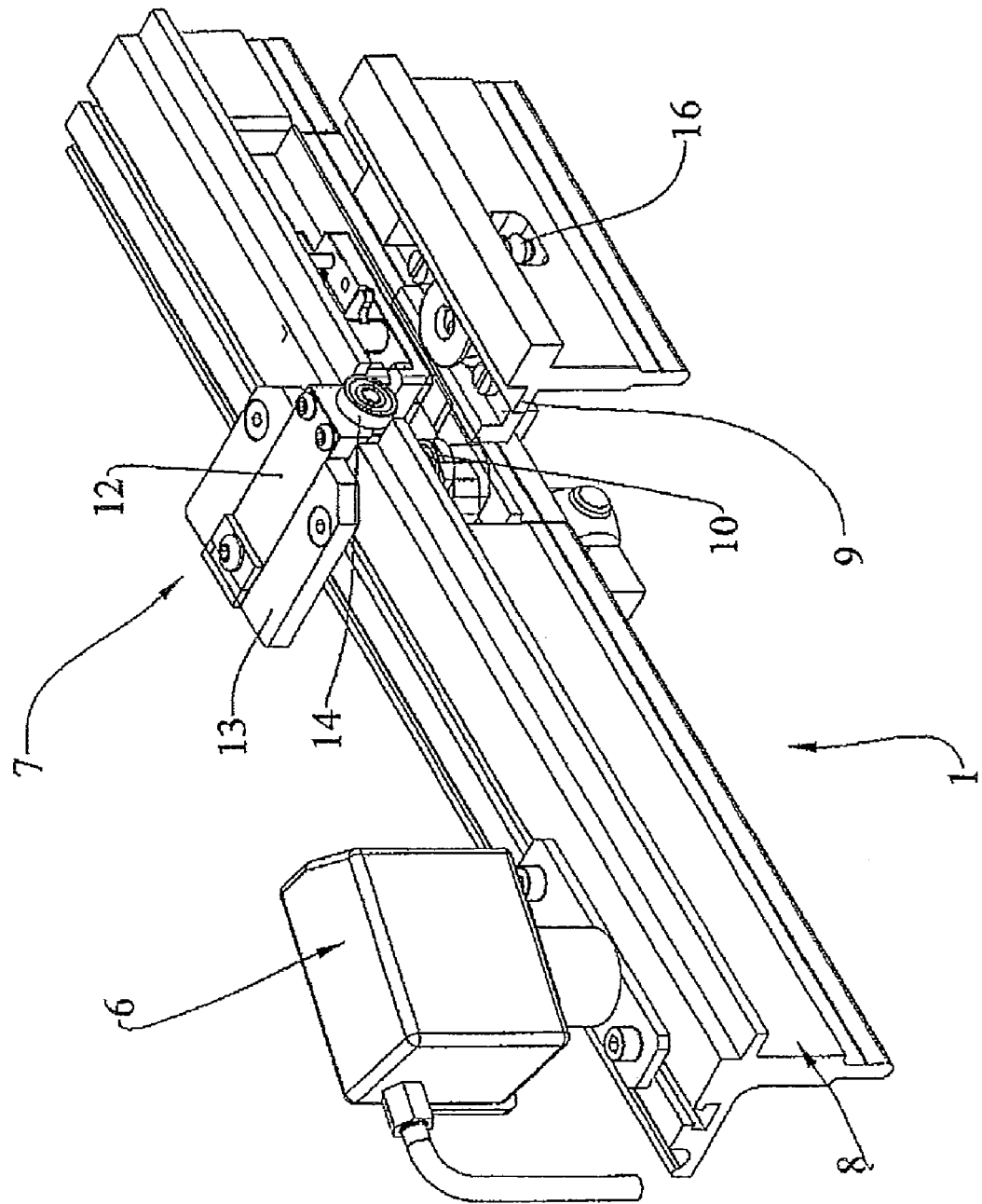
FIG. 2 is a perspective fragmented view of the same conveyor portion
Figure 3:
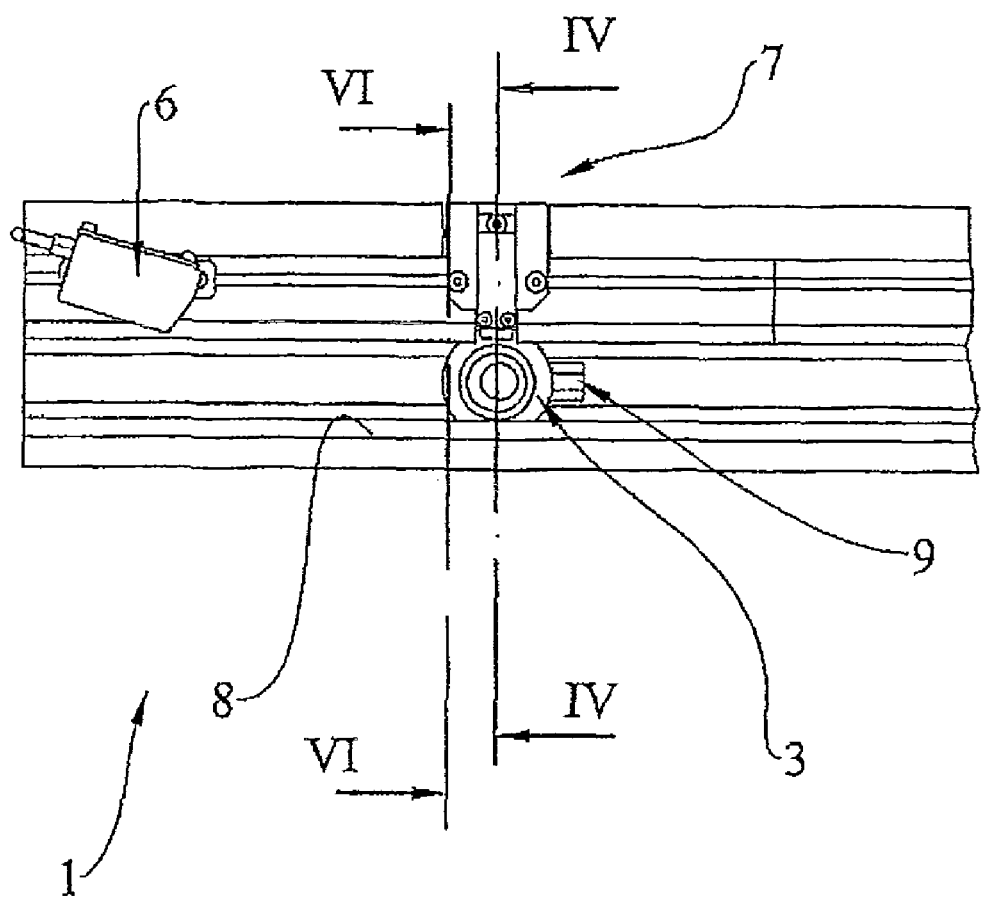
FIG. 3 is a top view of the conveyor portion of FIG. 1.

FIGS. 1-3 show part of a conveyor belt system 1 for specimen containers 2 (only one shown in the drawing) supported by respective carriers 3 made advancing along guides 8 by a conveyor belt 4. Along the conveyor belt 4 a container carrier turning device 7 is arranged in a defined position.

The container 2 is provided with a barcode 5 readable by a barcode reader 6 placed and oriented in a well defined position on the conveyor belt system.

The container carrier turning device 7 comprises a carrier stopping bearing 10 and a carrier pressing bearing 14 which can respectively engage a lateral surface 21 and an upper surface 20 of the container carrier 3.

Figure 4:
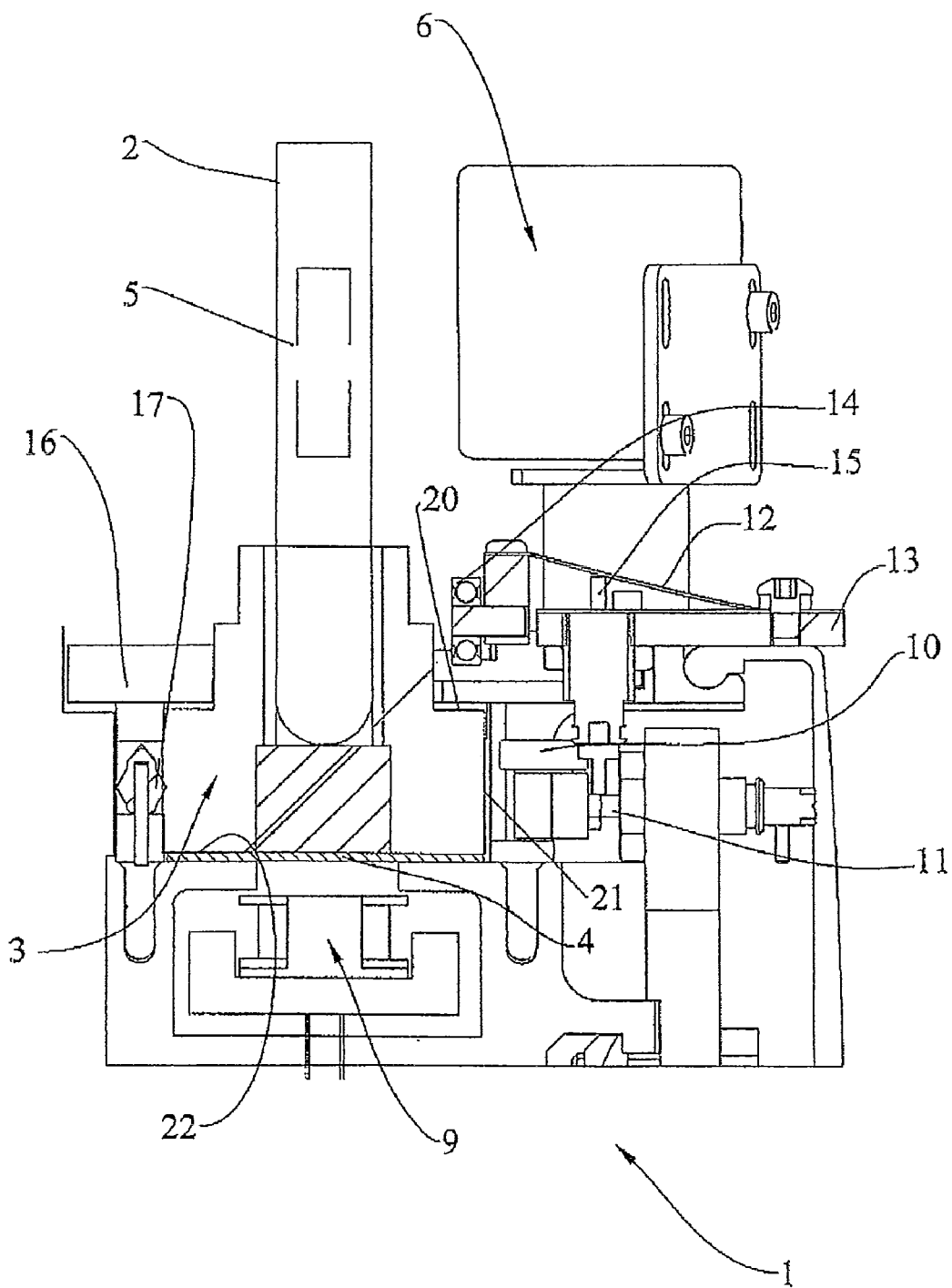
FIG. 4 is a sectional view along line IV-IV of FIG. 3 with the turning device in non-operating position.
Figure 5:
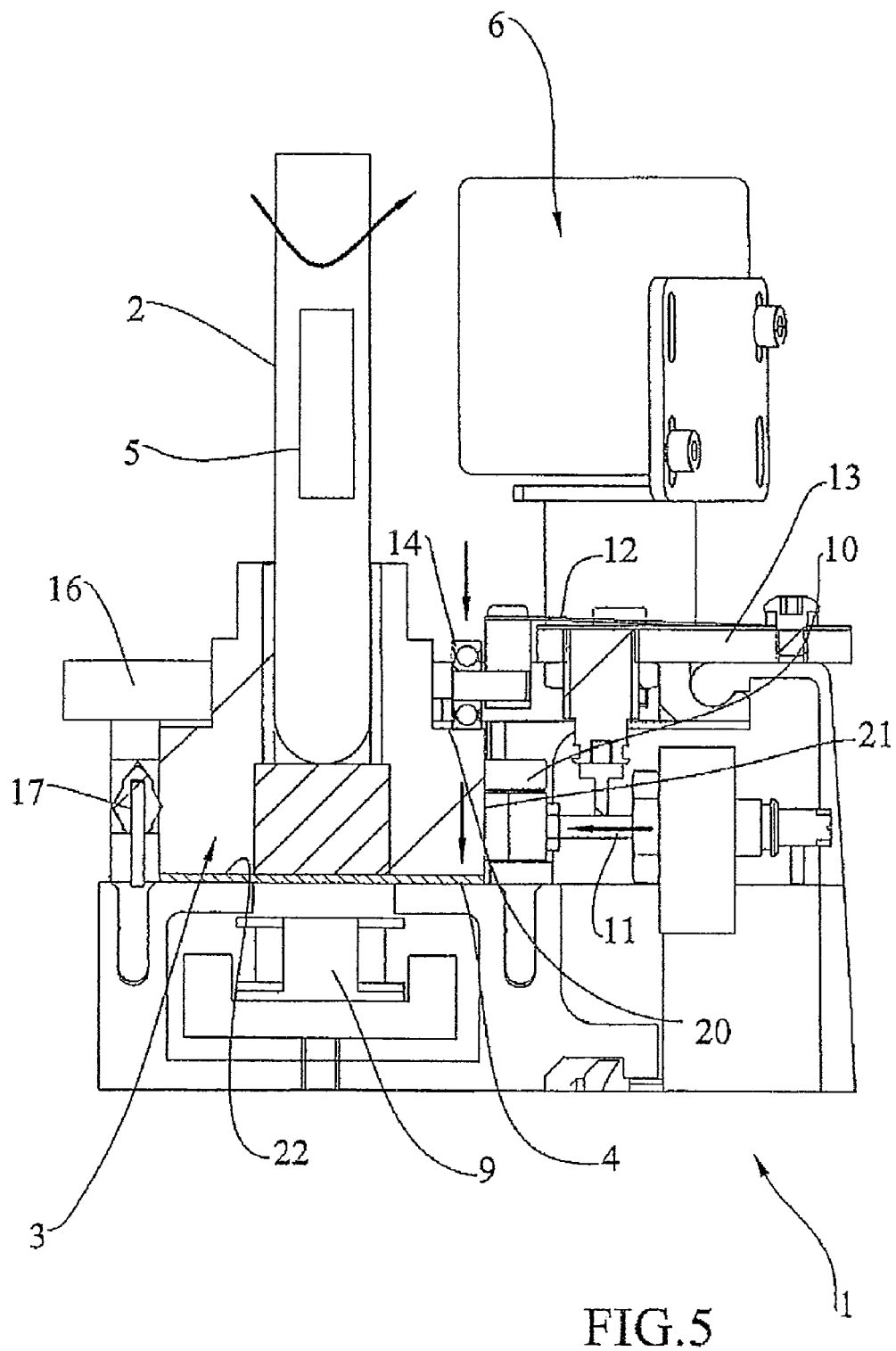
FIG. 5 is a sectional view similar to the one of FIG. 4 but with the turning device in operating position.
Figure 6:
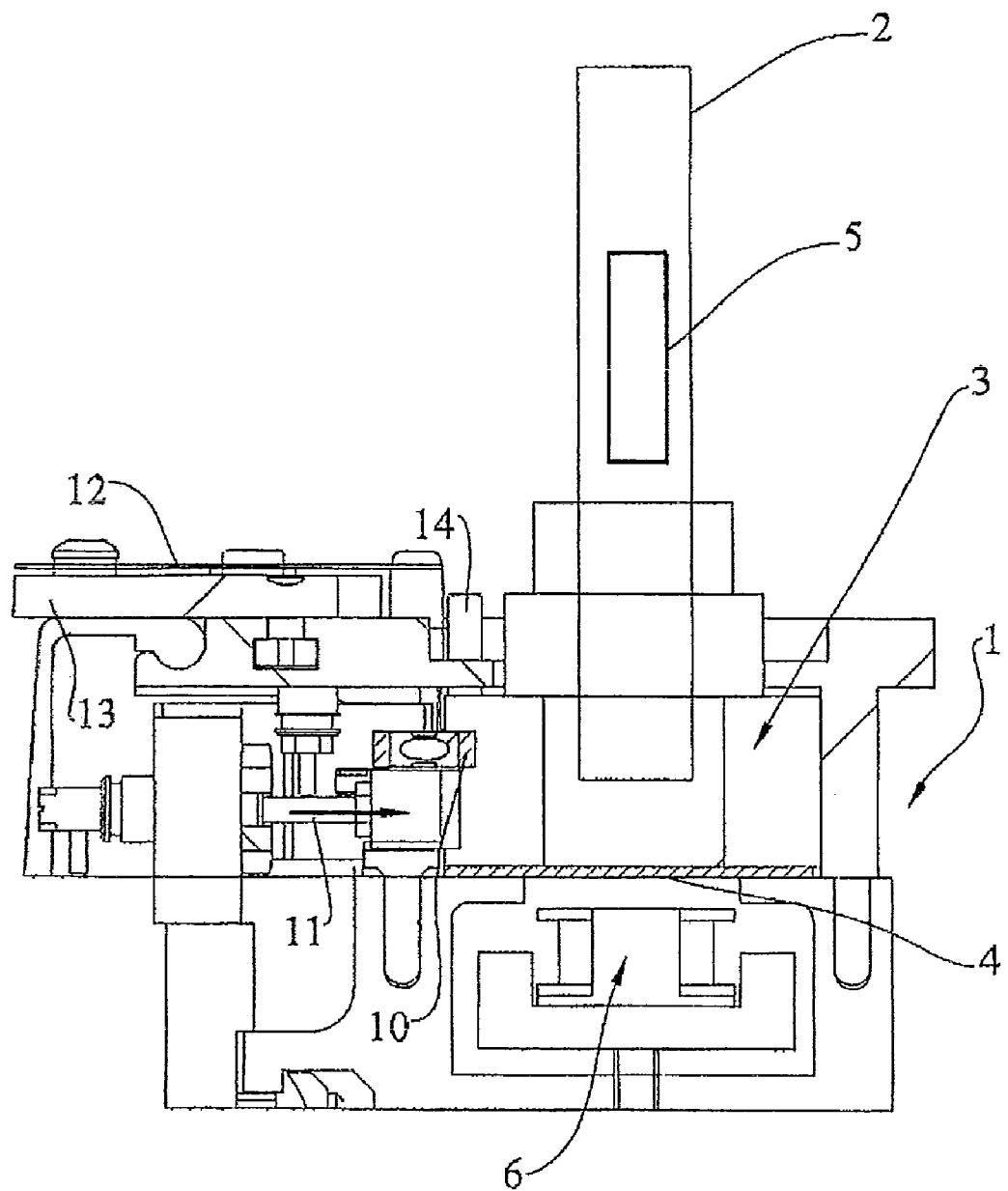
FIG. 6 is a sectional view along line VI-VI of FIG. 3.

The stopping bearing 10 is supported by a pneumatic piston 11 which move it between the disengaging position of FIG. 4 to the engaging position of FIGS. 5 and 6, in which the stopping bearing 10 is in contact with the lateral surface of the container carrier 3 to stop its advancement on the conveyor belt 4 while leaving it flee to rotate around the vertical axis of the container 2.

The pressing bearing 14 is supported by one end of an elastic plate 12 which has the other end fixed to a supporting frame 13. A pneumatic piston 15 is able to maintain the elastic plate 12 in the deformed raised position of FIG. 4, in which the pressing bearing 14 is not in contact with the upper surface 20 of the container carrier 3, and to allow the elastic plate 12 to move elastically to the non-deformed position of FIGS. 5 and 6, in which the pressing bearing 14 rotatably engages the upper surface 20 of the container carrier 3 to push the carrier towards the moving belt 4, underneath the container carrier.

The conveyor 1 is also provided with a pin 17 which supports an idle roller 16.

In operation, the carrier stopping means 10-11 are in the closed position with the turning device 7 in the rest position of FIG. 4. A detecting sensor 9, particularly an RFID antenna (Radio Frequency Identification Device) capable to read a tag inserted into the container carrier, is placed under the conveyor belt that supports the carrier 3 to notify to a control unit that a carrier 3 is arrived in position. The control unit, that has been notified by the RFID device that a carrier is in position having read the carrier ID, actuates the pneumatic piston 15 which was keeping elastically deformable member 12, causing the lowering of the pressing bearing 14 until engaging the upper surface 20 of the carrier 3 (FIGS. 5 and 6).

The friction between the belt 4 and the lower surface 22 of the carrier 3 therefore increases so that the advancement of the belt 4 in combination with the lateral engagement of the stopping bearing 10 causes the carrier 3 to turn around the vertical axis of the container 2. The idle roller 16 favours said turning.

As a result of the rotation of the container carrier 3 the container barcode 5 becomes readable by the barcode reader 6.

After reading, the pressing bearing 14 is moved upwards by the piston 15, which overcomes the elastic force of the elastic plate 12, and the stopping piston 11 is moved far from the carrier 3.

The carrier 3 thus stops rotating and is ready to be released by the stopping device 10 so being free to move forward on the belt 4.

Two pneumatic pistons 11 and 15 and the elastic force of the elastic plate 12 are sufficient for the operation of the carrier turning device 7.

No driving motor is provided.

The invention claimed is:

1. Container carrier turning device for a specimen container provided with an identifying barcode and inserted into a carrier made advancing by a conveyor belt, comprising carrier stopping means for rotatably engaging a lateral surface of said carrier to stop the advancing movement of the carrier while leaving it free to rotate around the container axis, carrier pressing means for rotatably engaging an upper surface of said carrier, elastic means for forcing said carrier pressing means to a carrier engaging position, first pneumatic means for moving said carrier stopping means to a carrier stopping position and second pneumatic means for moving said carrier pressing means to a carrier disengaging position against the action of said elastic means, characterized in that said elastic means includes an elastic plate fixed at one end to a supporting frame and supporting a pressing bearing, said pressing bearing being selectively movable with respect to said frame by a pneumatic piston directly actuating a deformation of the elastic plate, between a raised deformed position in which the pressing bearing is not in contact with the upper surface of the carrier, and a lower position in which the pressing bearing rotatably engages the upper surface of the carrier pushing the carrier towards the conveyor belt providing the rotation of the carrier, an idle rotatable bearing being provided opposite to the pressing bearing to facilitate the carrier rotation when the elastic means applies its force to the upper part of the carrier.

2. Device according to claim 1, characterized in that the carrier turning device is associated to an RFID reader capable to identify the container carrier presence through the reading of a tag thereof.

* * * * *